US009784606B2

(12) United States Patent
Ahmed et al.

(10) Patent No.: US 9,784,606 B2
(45) Date of Patent: Oct. 10, 2017

(54) TWO-PHASE FLOW DETECTOR USING HEAT TRANSFER IN CROSS FLOW

(71) Applicant: King Fahd University of Petroleum and Minerals, Dhahran (SA)

(72) Inventors: Wael Hasan Ahmed, Guelph (CA); Hassan Mohamed Badr, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 139 days.

(21) Appl. No.: 14/947,293

(22) Filed: Nov. 20, 2015

(65) Prior Publication Data
US 2017/0146379 A1    May 25, 2017

(51) Int. Cl.
G01F 1/74 (2006.01)
G01F 1/68 (2006.01)
G01F 1/688 (2006.01)

(52) U.S. Cl.
CPC .............. *G01F 1/6888* (2013.01); *G01F 1/74* (2013.01)

(58) Field of Classification Search
CPC ........................................................ G01F 1/74
USPC ........................................................ 73/61.74
See application file for complete search history.

(56) References Cited

U.S. PATENT DOCUMENTS

2016/0313160 A1* 10/2016 Ueberschlag ........ G01N 29/024

FOREIGN PATENT DOCUMENTS

CN         101539016 A     9/2009

OTHER PUBLICATIONS

Liu et al. Translation of cn101539016. Published Apr. 21, 2009. Translated May 30, 2017.*
H. M. Badr, "A Theoretical Study of Laminar Mixed Convection From a Horizontal Cylinder in a Cross Stream", Int. J. Heat Mass Transfer, vol. 26, No. 5, 1983, pp. 639-653.
H. M. Badr, "Effect of free-stream fluctuations on laminar forced convection from a straight tube", Int. J. Heat Mass Transfer, vol. 40, No. 15, 1997, pp. 3653-3662.

* cited by examiner

*Primary Examiner* — Walter L Lindsay, Jr.
*Assistant Examiner* — Philip Marcus T Fadul
(74) *Attorney, Agent, or Firm* — Oblon, McClelland, Maier & Neustadt, L.L.P.

(57) ABSTRACT

A temperature sensing device comprising a plurality of thermocouples in a hollow tube, where the thermocouples sensing tips contact the outer wall of the tube, and a heat flux source that heats the hollow tube. The hollow tube is inserted through a cross section of a pipe perpendicular to the longitudinal axis of the pipe. The apparatus measures a void fraction in a two-phase flow of a liquid-gas mixture flowing through the pipe. A process of measuring void fraction whereby the hollow tube is heated to an initial temperature, and in the presence of a liquid-gas mixture flow through the pipe the difference is calculated between the initial temperature of the tube and the temperature during liquid-gas mixture flow, to determine the void fraction in the two-phase flow of liquid-gas mixture through the pipe.

16 Claims, 7 Drawing Sheets

TWO-PHASE FLOW DETECTOR USING HEAT TRANSFER IN CROSS FLOW

BACKGROUND OF THE INVENTION

Technical Field

The present invention relates to a device which employs thermocouples to determine a void fraction of a two-phase flow of a liquid-gas mixture in a pipe.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The need for multiphase flow measurement in the oil & gas production and petrochemical industries became prominent in recent years. A number of multiphase flow meters were developed during the last few years by research organizations, meter manufacturers, and oil & gas production companies. These meters use different technologies and the prototypes are varied in design and function.

Reliable measurements of the multiphase flow parameters such as void fraction, phase concentration, phase velocity and flow pattern identification are important for accurate modeling of multiphase systems. These parameters can be measured using a number of techniques, including radiation attenuation (X-ray, gamma-ray or neutron beams) for line or area averaged values, optical or electrical contact probes for local void fraction, impedance technique using capacitance sensors and direct volume measurement using quick-closing valves. The selection of the proper technique depends on the application, and whether a volumetric average or a local void fraction measurement is desired. Accurate measurement of the liquid and gas fractions, also known as void fractions, is essential to the the oil and gas industry, as well as the nuclear energy and chemical processing industries.

Meters from different manufacturers vary in their design, function and capabilities. In the oil industry, the measurement of oil and water flow rate in each production zone of an oil well is very important to monitor and control the fluid movement in the well and reservoir. Therefore, numerous research efforts have been carried out designing accurate multiphase flow meters. A variety of meters are currently under development worldwide. Most of these are equipped with a static mixer or a T-elbow to homogenize the multiphase flow, then the flow rate of each phase is measured using a combination of Gamma-ray densitometer, capacitance water cut meter and cross-correlation type flow meter. However, there are technical challenges in the operation of some of these meters. For example, meters equipped with gamma densitometers that utilize a nuclear source are widely used for measuring the fluid density. The primary drawback of these meters is the environmental and safety issues associated with the nuclear sources.

The Coriolis sensor measures both the mass flow and density by tracking the natural frequency of the vibrating pipe carrying the fluid. These devices, however, require a vibration source which makes them mechanically complex and relatively difficult to maintain.

Optical sensors employing fiber optics have demonstrated high accuracy in addition to being neither intrusive nor invasive, however these sensors are restricted when it comes to monitoring opaque fluids.

Finally, thermal mass flow meters generally use combinations of heated elements and temperature sensors to measure the difference between static and flowing heat transfer to a fluid and infer its flow with knowledge of the fluid's specific heat and density. If the density and specific heat characteristics of the fluid are constant, the meter can provide direct mass flow readout, and does not need any additional pressure temperature compensation over their specified range.

The idea behind using thermal conductivity for the measurement of void fraction in two-phase flows is the sensitivity of heat convection from a solid body to the properties of the flowing fluid (especially the thermal conductivity). It is well established that the rate of heat transfer from a heated cylinder placed in a fluid stream depends on the fluid properties as well as free stream temperature, velocity of the approaching stream, cylinder geometry including surface roughness, cylinder surface temperature, and flow structure of the oncoming stream. The detailed analysis of the heat transfer process from a cylinder in cross flow has been the subject of numerous research investigations [H. M. Badr, "A theoretical study of laminar mixed convection from a horizontal cylinder in a cross-stream", International Journal of Heat and Mass Transfer, Vol. 26, No. 5, pp. 639-653, 1983; H. M. Badr, "On the effect of flow direction on mixed convection from a horizontal cylinder," International Journal for Numerical Methods in Fluids Vol. 5, pp. 1-12, 1985; H. M. Badr, "Effect of free-stream fluctuations on laminar forced convection from a straight tube", International Journal of Heat and Mass Transfer, Vol. 40, No. 15, pp. 3653-3662, 1997; S. Whitaker, "Forced convection heat transfer correlations for flow in pipes, past flat plates, single cylinders, single spheres, and for flow in packed beds and tube bundles", AIChE Journal, Volume 18, Issue 2, pages 361-371, 1972; B. G. Hegge Zijnen, "Heat transfer from horizontal cylinders to a turbulent air flow", Appl. Sc. Res., Section A, Vol. 7, pp. 205-223, 1958—Each incorporated herein by reference in its entirety], covering various modes of heat transfer such as constant surface temperature and constant heat flux, along with structures of the approaching stream (laminar and turbulent flow regimes).

In view of the forgoing, the objective of the present invention is to provide an apparatus involving a hollow tube with a plurality of thermocouples for measuring the void fraction of a two-phase flow in a pipe.

BRIEF SUMMARY OF THE INVENTION

According to a first aspect, the present disclosure relates to an apparatus including (i) a temperature sensing device comprising a plurality of thermocouples having a sensing tip and wiring that is connected to a potentiometer, (ii) a hollow tube, wherein the sensing tip of the thermocouples pass through the inner wall of the hollow tube and extend radially from the hollow tube to contact the outer wall at different locations along the length of the hollow tube, (iii) a heat flux source that is connected to the hollow tube, wherein the heat flux source heats the walls of the hollow tube. The hollow tube is inserted through a cross section of a pipe perpendicular to a longitudinal axis of the pipe such that no more than 80% of the hollow tube is within the interior of the pipe relative to the total length of the hollow tube. The apparatus measures a void fraction in a two-phase flow of a liquid-gas mixture flowing through the pipe.

In one embodiment, the ratio of the hollow tube outer diameter to inner diameter is at least 3:2 and a ratio of the hollow tube longitudinal length to outer diameter is at least 39:4 and a ratio of the inner diameter of the hollow tube to the inner diameter of the pipe is at least 1:3.

In one embodiment, the hollow tube is at least 1 inch in diameter.

In one embodiment, the hollow tube is threaded and secured to the pipe by a threaded coupling fitting.

In one embodiment, at least a portion of the hollow tube is covered by a thermal insulation material.

In one embodiment, the wiring of the thermocouple is aligned with the longitudinal axis of the hollow tube and flush with the interior wall of the hollow tube.

In one embodiment, the wiring of the thermocouple is insulated.

In one embodiment, the apparatus includes an external thermocouple located outside of the hollow tube and within the interior of the pipe that measures the external temperature of the tube.

In one embodiment, the apparatus has at least 4 thermocouples.

In one embodiment, the heat flux source produces at least 0.5 kW of power.

In one embodiment, the apparatus also includes an electronics housing unit comprising the potentiometer connected to the thermocouples and a heat flux controller connected to the heat flux source.

In one embodiment, the apparatus also includes a computer connected to the potentiometer and the heat flux controller.

In one embodiment, the two-phase liquid-gas mixture is selected from a group comprising a hydrocarbon, a heat transfer fluid, water, or a combination thereof.

According to a second aspect, the present disclosure relates to a method of measuring void fraction including (i) heating the hollow tube of claim 1 to a temperature in the range of 20° C.-34° C. to form a heated hollow tube, (ii) recording a baseline temperature measurement on the outer surface of the heated hollow tube before liquid-gas mixture flow through the pipe and a temperature measurement from the plurality of thermocouples on the outer wall of the heated hollow tube in the presence of liquid-gas mixture flow through the pipe, (iii) calculating the difference between the initial baseline temperature and the temperature measurement in the presence of liquid-gas mixture flow, and (iv) determining the void fraction in the two-phase flow of liquid-gas mixture through the pipe based on the calculated difference.

In one embodiment, the calculating includes averaging the temperature measurements of the outer wall of the hollow tube from the plurality of thermocouples.

In one embodiment, the temperature measurement is recorded after a stable temperature is reached. In one embodiment, the determining comprises correlating the temperature difference to the void fraction from a curve of temperature difference as a function of void fraction.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
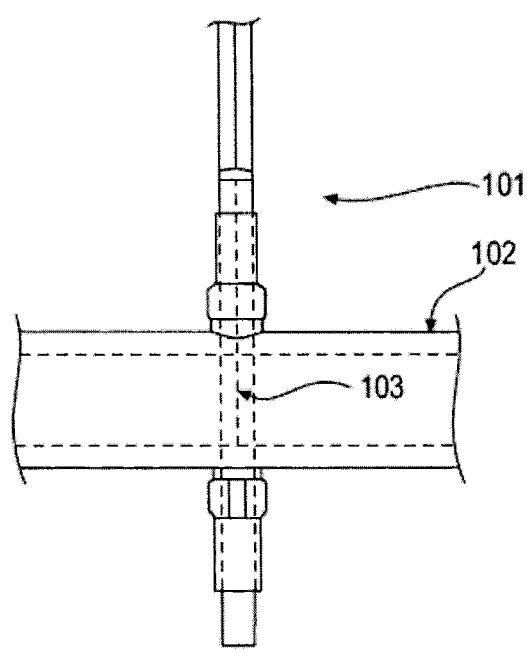
FIG. 1 is a schematic of an exemplary apparatus 101 placed inside an exemplary pipe 102. The location of the thermocouples 103 is indicated within the apparatus.
Figure 2:
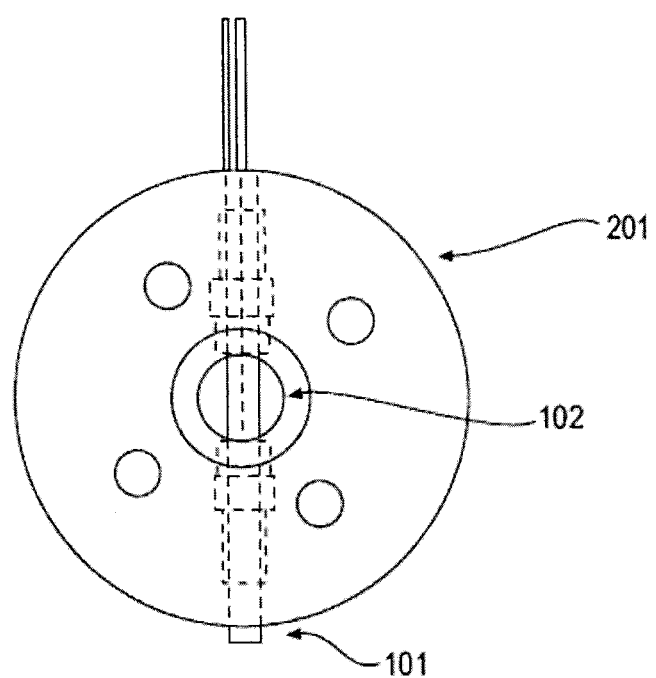
FIG. 2 is an alternate view of an exemplary apparatus 101 placed inside an exemplary pipe 102. A view of the flanges of the exemplary pipe 201.
Figure 3:
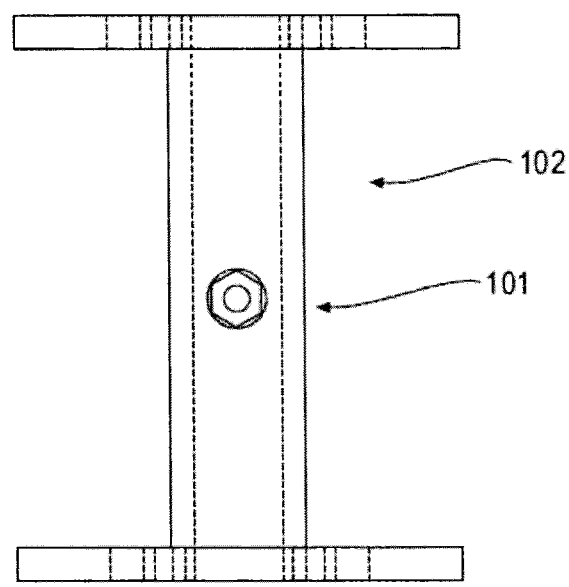
FIG. 3 is an alternate view of an exemplary apparatus 101 placed inside an exemplary pipe 102.
Figure 4:
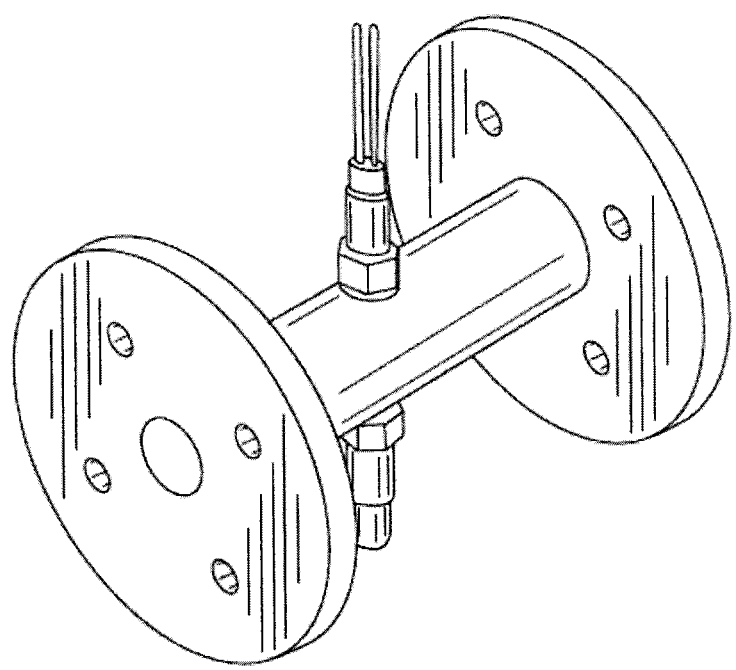
FIG. 4 is an alternate view of the apparatus.

Referring now to the drawings, wherein like reference numerals designate identical or corresponding parts throughout the several views.

According to a first aspect, the present disclosure relates to an apparatus, depicted in FIG. 1-5 including a temperature sensing device comprising a plurality of thermocouples having a sensing tip and wiring that is connected to a potentiometer. The thermocouple is composed of two conducting wires that are capable of transmitting a voltage as a function of a thermal gradient across the junction of the two wires. This phenomenon is known as the thermoelectric effect. The voltage can be converted to a temperature readout by a calibrated potentiometer. Since the wire is conductive, the thermocouple is designed such that the wire exposed to a thermal gradient is limited to a region referred to as the sensing tip of the thermocouple. Limiting the exposure of the wire is accomplished by insulating the wire not included in the sensing tip with a chemical resistant thermal insulator. This insulation mitigates the potential intervention by thermal noise from the surrounding environment. The sensing tip may be adapted to contact a specimen to obtain a temperature measurement.

The present disclosure relates to a hollow tube in cylindrical form, as shown in FIG. 1, employed in the temperature sensing device 101, however the shape of the hollow tube may be, but is not limited to a cuboid, an ellipse, a polyhedral (n-gonal prism), an oblique or a parabaloid. In one embodiment, the hollow tube is made from a thermally conductive material. The thermally conductive material may be, but is not limited to copper, steel, aluminum, or combinations thereof. In one embodiment, the hollow tube is formed from a single cylinder (i.e. the hollow tube is not segmented). In one embodiment, the hollow tube is formed from concentric tubes configured together to form a larger tube structure. In an alternative embodiment, the hollow tube is formed from nested concentric tubes configured to extend telescopically to form a continuous tube structure.

In one embodiment, the ratio of the dimensions of the hollow tube outer diameter to inner diameter is at least 2:1, at least 5:3, at least 3:2, at least 4:3, at least 5:4. In a preferred embodiment, the inner diameter of the hollow tube is at least 0.5 inches, at least 1 inch, at least 3 inches, at least 5 inches. The ratio of the hollow tube longitudinal length to outer diameter is at least 4:1, at least 5:1, at least 6:1, at least 8:1, at least 10:1.

As depicted in FIG. 1, the hollow tube 101 is inserted through a cross section of a pipe 102 perpendicular to the longitudinal axis of the pipe such that no more than 90%, no more than 80%, no more than 70%, no more than 60%, no more than 50%, no more than 40%, no more than 30%, no more than 20%, no more than 10% of the hollow tube is within the interior of the pipe relative to the total length of the hollow tube. In one embodiment, the ratio of the inner diameter of the hollow tube to the inner diameter of the pipe is at least 1:5, at least 1:4, at least 1:3, at least 1:2, at least 3:5, at least 2:3, at least 3:4, at least 4:5.

In one embodiment, the hollow tube is placed in a cross section of the pipe in a configuration perpendicular to the longitudinal axis of the pipe, in which the tube is secured to the pipe and extends across the diameter of the cross section. This configuration is preferred to measure void fraction in straight sections of pipe, but may also be employed in curved pipe sections.

It is also envisaged that the present apparatus can be modified such that the hollow tube bisects the pipe in a non-perpendicular configuration and still function as intended. For example, in one embodiment, the hollow tube is placed in a cross section of the pipe in an oblique configuration to the longitudinal axis of the pipe (i.e. neither perpendicular to nor parallel to the longitudinal axis). In this scenario, the tube may be configured at an angle less than 90°, less than 60°, less than 45°, less than 30°, or less than 20°, and greater than 0° relative to the longitudinal axis of the pipe. This oblique configuration may be used for straight section of pipe, or preferably in curved sections of pipe.

The hollow tube may be placed in the cross section of the pipe by different configurations such as, but not limited to a guided track system along the wall of the pipe and parallel to the longitudinal axis of the pipe to allow mobility of the hollow tube along the longitudinal axis of the pipe, two guided tracks diametrically opposite in a cross section of the pipe that allow the hollow tube to move along the diameter of the pipe, or held between two staggered guided tracks diametrically opposite in a cross section of the pipe to allow for non-perpendicular configurations relative to a longitudinal axis of the pipe. Configurations listed above can be useful to measure void fractions in regions of pipe with multi-directional fluid flow.

In one embodiment, a plurality of hollow tubes are arranged coplanar around the inner circumference of the pipe like spokes in a cross section of the pipe. In another embodiment, a plurality of hollow tubes are arranged as parallel cords across a cross section of a pipe. In an alternative embodiment a plurality of hollow tubes are arranged in parallel planes along the longitudinal axis of the pipe while intersecting a radial plane of the pipe at 90°. In another embodiment, a plurality of hollow tubes are arranged in parallel planes along the longitudinal axis of the pipe while intersecting a radial plane of the pipe at less than 90°, less than 60°, less than 45°, less than 30°, or less than 20° relative to the radial plane of the pipe.

Figure 5:
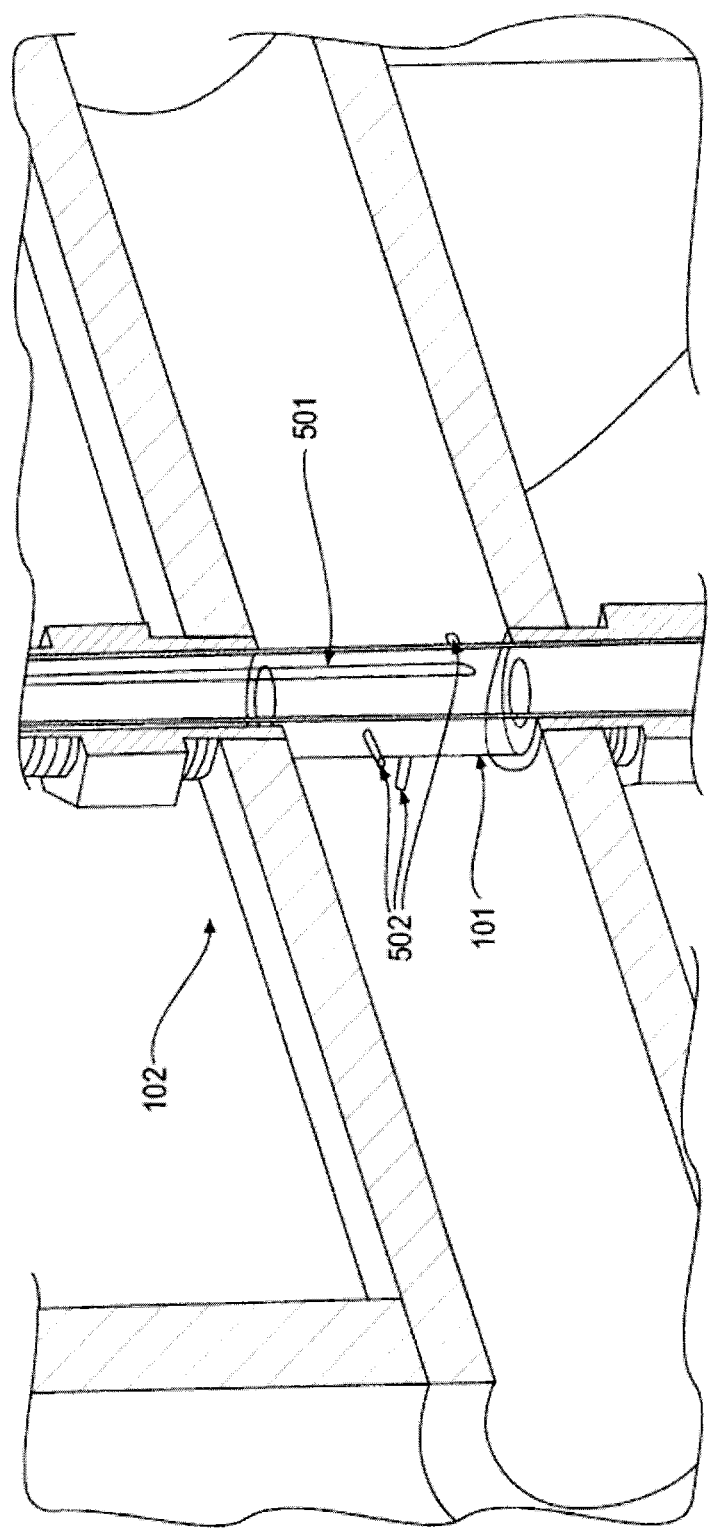
FIG. 5 is a close-up illustration of an exemplary apparatus 101 within an exemplary pipe 102, with a view of a thermocouple 501 and thermocouple sensing tips 502.

FIG. 5 depicts one embodiment of the apparatus in which the hollow tube is threaded and secured to the pipe by a threaded coupling fitting. It is envisaged that the hollow tube can also be affixed to the pipe by additional attachments such as, but not limited to clamping, welding, or brazing. In one embodiment, at least a portion of the hollow tube is covered by a thermal insulation material. In a preferred embodiment, the portion of the hollow tube outside the pipe is covered by a thermal insulation material. A thermal insulation material may be, but is not limited to fiberglass, rock wool, calcium silicate, cellular glass, foam, vermiculite. The portion of the hollow tube exposed to the environment outside the pipe and the attachment joint are advantageously covered by a thermal insulation material to prevent external environmental conditions from intervening in the temperature measurement of the portion of the pipe within the hollow tube.

In the present disclosure the hollow tube walls are heated by a heat flux source that is connected to the hollow tube. A heat flux source provides heat to the hollow tube for the baseline temperature measurement and throughout the apparatus operation. The heat flux source may be configured into the wall of the hollow tube, inside the hollow tube, or along the outside wall of the hollow tube. In one embodiment, the heat flux source is an electric heating element. In an alternative embodiment, the heat flux source comprises an inductive heating unit and a power source. In one embodiment, the heat flux source produces at least 0.25 kW, at least 0.5 kW, at least 1 kW, at least 10 kW, at least 25 kW, at least 50 kW, at least 100 kW. In one embodiment, the apparatus also includes a heat flux controller that is electrically connected to the heat flux source and controls the voltage and overall power output from the heat flux source, which in turn controls the temperature of the walls of the hollow tube.

In one embodiment of the present disclosure, the hollow tube contains at least 2, at least 4, at least 6, at least 8, at least 10, at least 15, at least 20 thermocouples. As FIG. 5 depicts, in one embodiment, the wiring of the thermocouple 501 is aligned with the longitudinal axis of the hollow tube and is flush with the interior wall of the hollow tube. As used herein, the term "flush" refers to the wiring being directly adjacent to and even with the interior wall of the hollow tube. The wiring of the thermocouple may be insulated with a thermal insulation material to prevent heat transfer from the inner wall of the hollow tube to the thermocouple wiring and to prevent heat loss from the thermocouple wiring to an external environment (e.g. within the hollow tube, outside of the pipe, etc.). A thermal insulation material used to insulate the thermocouple wiring may be, but is not limited to a mineral insulated metal sheath, silicone, or perfluoroalkoxy alkanes. FIG. 5 depicts the sensing tips of the thermocouples 502 passing through the inner wall of the hollow tube and extending radially from the hollow tube to contact the outer wall at different locations along the length of the hollow tube that is within the pipe. The sensing tips can be positioned at various angles relative to the longitudinal axis, whereby 0° angle is a straight configuration between the thermocouple wiring and the sensing tip, and 180° is a 'U' or anti-parallel configuration whereby the thermocouple tip is turned toward the wiring. The sensing tips can be positioned at various angles relative to the longitudinal axis of the hollow tube between 0°-180°, preferably between 20°-160°, preferably between 30°-140°, preferably between 50°-120°, or preferably between 70°-100°. In a preferred embodiment, the sensing tips pass through the inner wall of the hollow tube at an angle about 90° relative to the longitudinal axis of the hollow tube. In a preferred embodiment, the sensing tips may be oriented in any direction within the 360° circumference of the outer wall of the hollow tube. In another embodiment the thermocouples are arranged in a pattern around the circumference of the hollow tube such that the tube is ringed with thermocouple sensing tips along the length of the hollow tube. The thermocouple tips may be passed through the hollow tube inner wall to contact the outer wall using an attachment that includes threading through a corresponding threaded port, a compression fitting, a clamp, a polymer seal, and the like. In one embodiment, the ratio of the thermocouple tip diameter to the hollow tube diameter is at most 1:2, at most 1:3, at most 1:4, at most 1:8, at most 12:125, at most 1:32, at most 1:100, at most 1:500, at most 3:1000.

In one embodiment, the thermocouple sensing tips extend from the outer wall of the hollow tube by at least 3 lengths of the hollow tube outer diameter, at least 2 lengths of the hollow tube outer diameter, at least 1 length of the hollow tube outer diameter, and at least 0.5 lengths of the hollow tube outer diameter.

In one embodiment the apparatus includes an external thermocouple having at least one sensing tip that measures the external temperature of the tube for reference. The external thermocouple can be attached to the exterior of hollow tube and wired through the wall of the hollow tube (similarly wired as the thermocouples for measurement of the outer wall of the tube), but the sensing tip only contacts the external environment of the hollow tube and not the tube itself. One purpose of the external thermocouple is to reference the external environment (i.e. temperature) to the hollow tube but within the pipe. Irregular temperatures due to environmental fluctuations may adversely affect the apparatus and its accuracy may therefore be recorded.

In one embodiment the apparatus also includes an electronics housing unit (EHU) comprising the potentiometer connected to the thermocouples and a heat flux controller connected to the heat flux source. The potentiometer may be configured to connect directly or wirelessly with the thermocouples. Similarly, the heat flux controller may be configured to connect directly or wirelessly with the heat flux source. The EHU may be affixed to the portion of the hollow tube outside the pipe or as a separate unit connected to the thermocouples and the heat flux source either directly or wirelessly.

In one embodiment the apparatus also includes a computer connected to the potentiometer and the heat flux controller. The computer can be connected directly or wirelessly to the potentiometer and the heat flux controller. The computer can be located on the apparatus or at another location and capable of communicating wirelessly by known communication networks such as, but not limited to satellite and cellular networks.

Figure 7:
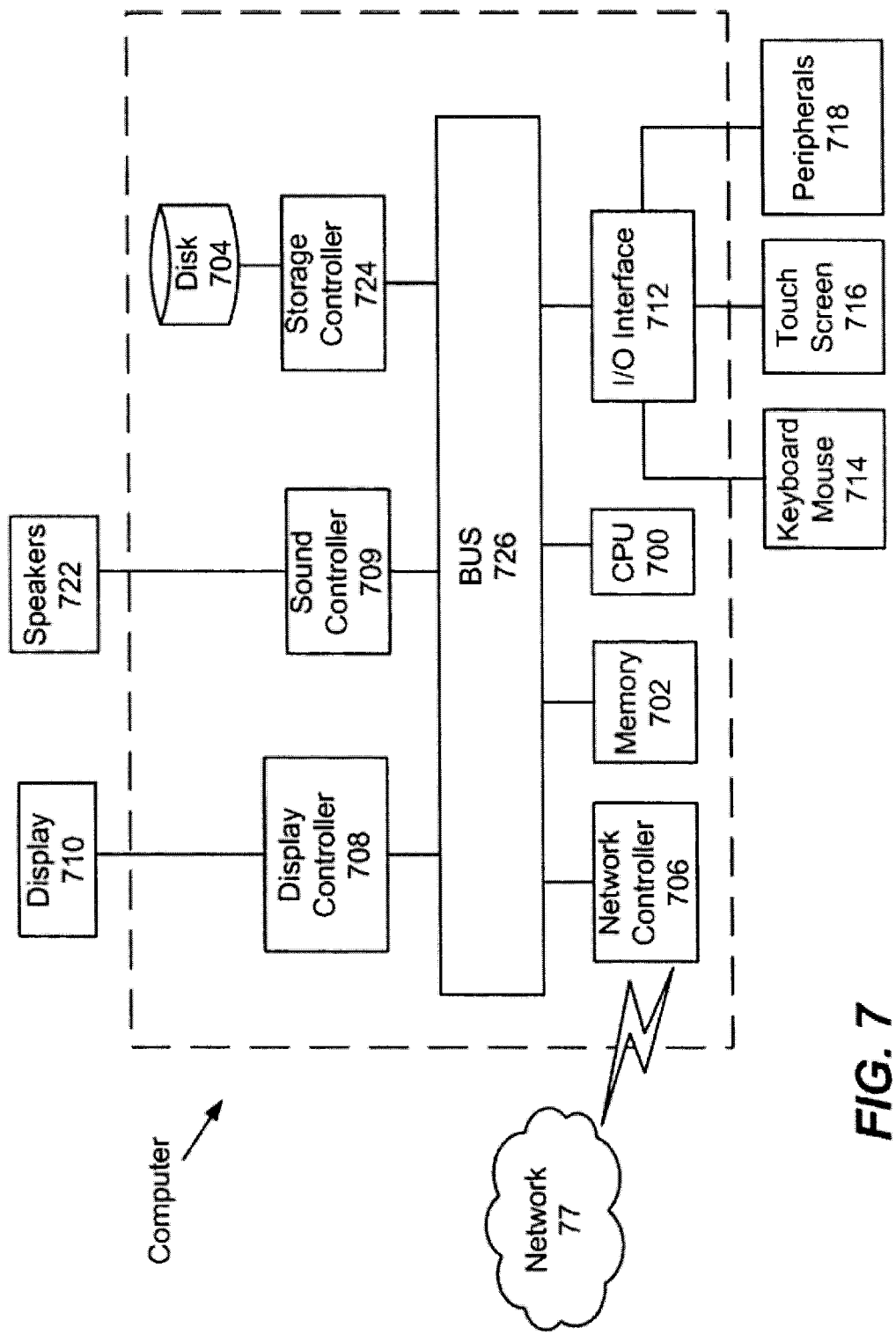
FIG. 7 is a schematic of a computer, hardware, components, and connections to the apparatus heat flux controller and potentiometer.

Next, a hardware description of the computer according to exemplary embodiments is described with reference to FIG. 7. In FIG. 7, the computer includes a CPU 700 which performs the processes described above/below. The process data and instructions may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer communicates, such as a server or computer.

Further, the claimed advancements may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

The hardware elements in order to achieve the computer may be realized by various circuitry elements, known to those skilled in the art. For example, CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

The computer in FIG. 7 also includes a network controller 706, such as an Intel Ethernet PRO network interface card from Intel Corporation of America, for interfacing with network 77. As can be appreciated, the network 77 can be a public network, such as the Internet, or a private network such as an LAN or WAN network, or any combination thereof and can also include PSTN or ISDN sub-networks. The network 77 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 518 including printers and scanners, such as an OfficeJet or DeskJet from Hewlett Packard.

A sound controller 709 is also provided in the computer, such as Sound Blaster X-Fi Titanium from Creative, to interface with speakers/microphone 722 thereby providing sounds and/or music.

The general purpose storage controller 724 connects the storage medium disk 504 with communication bus 726, which may be an ISA, EISA, VESA, PCI, or similar, for interconnecting all of the components of the computer. A description of the general features and functionality of the display 710, keyboard and/or mouse 714, as well as the display controller 708, storage controller 724, network controller 706, sound controller 709, and general purpose I/O interface 712 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

The above-described hardware description is a non-limiting example of corresponding structure for performing the functionality described herein.

Figure 6:
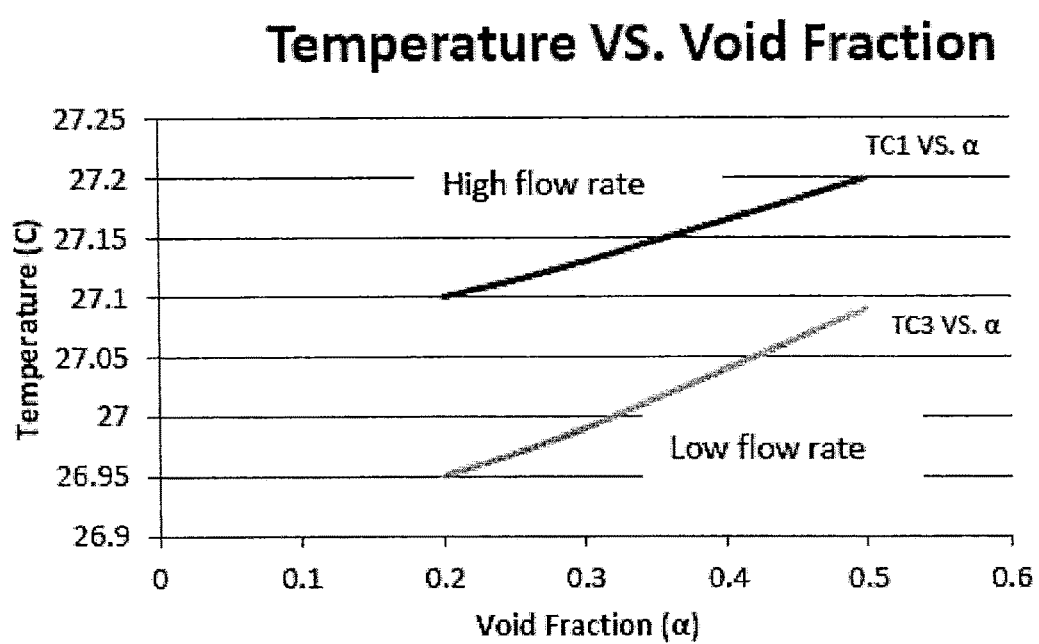
FIG. 6 is a line graph of the exemplary apparatus temperature as a function of void fraction at a high velocity of two-phase fluid flow rate and low velocity of flow of a two-phase fluid flow rate.

The apparatus of the present disclosure measures a void fraction in a two-phase flow of a liquid-gas mixture flowing through the pipe. A void fraction is defined as the fraction of the flow volume that is occupied by the gas phase. The two-phase flow is a particular example of multi-phase flow, wherein the two phases are gas and liquid separated by a meniscus. "Fluid" as used in this disclosure is defined as a substance that continually deforms under an applied shear stress and includes liquids, gases, plasmas, and some plastic solids. Two-phase flow can occur between two phases of a single fluid (steam and water, etc) or a mixture of fluids in two phases (air and water, etc). In the present disclosure the two-phase flow measurement exploits the difference in the rate of heat transfer from a heated solid placed in a liquid stream as opposed to a gaseous stream. The cooling of a solid surface by heat transfer is highly dependent on the physical properties and structure of the flowing gas/liquid mixture. If the gas content of a fluid is high, the surface temperature of a continuously heated solid submerged and in contact with the fluid flow will stabilize at a relatively high temperature because of the low thermal conductivity of the gas. However, if the liquid content of a fluid is high, then the surface temperature of a continuously heated solid submerged and in contact with the fluid flow will stabilize at a relatively lower temperature because of the higher thermal conductivity of the liquid. FIG. 6 depicts the relationship between temperature and void fraction in which the stabilization of the apparatus temperature is relatively high in the presence of relatively high void fraction, and stabilization of the apparatus temperature is relatively low in the presence of relatively low void fraction. In the present disclosure the hollow tube is heated and the thermocouples in the hollow tube register the outer wall temperature of the hollow tube in the presence of fluid flow. The plurality of the thermocouples along the radial length of the hollow tube ensure that a measurement is taken at intervals along the axial length of the pipe such that the fluid flow within the pipe cross section is recorded.

In one embodiment the two-phase liquid-gas mixture is selected from a group comprising a hydrocarbon, a heat transfer fluid, water, or a combination thereof. Examples of a hydrocarbon may be petroleum or natural gas. Examples of a heat transfer fluid may be propylene glycol, silicone oils, or mineral oils.

According to a second aspect, the present disclosure relates to a method of measuring void fraction. The method involves heating the hollow tube to a temperature in a range preferably within 10° C.-50° C., preferably within 15° C.-45° C., preferably within 20° C.-40° C., preferably within 25° C.-35° C. Next, recording a baseline temperature measurement on the outer surface of the heated hollow tube before liquid-gas mixture flow through the pipe. In this disclosure a "baseline temperature measurement" is the measurable temperature to which the hollow tube has been heated and has changed by no more than 1.0%, preferably no more than 0.5%, more preferably 0.1% for at least 1 minute. The method also involves, periodically recording a temperature measurement from the plurality of thermocouples on the outer wall of the tube in the presence of liquid-gas mixture flow through the pipe. For example, the recording rate may be at least 2/min, at least 4/min, at least 10/min, at least 30/min at least 1/s. The method also involves, calculating the difference in the baseline temperature of the hollow tube and the temperature measurement of the hollow tube during liquid-gas mixture flow. The method also involves, calculating the difference between the temperature of the hollow tube during two-phase flow and the baseline temperature. Finally, the method involves determining the void fraction in the two-phase flow of liquid-gas mixture through the pipe by comparing the calculated difference with graphical plots of standards for temperature change as a function of flow-rate and void fraction in two-phase flow.

In one embodiment, the calculating includes averaging the temperature measurements of the outer wall of the hollow tube from the plurality of thermocouples. Averaging is useful to reduce the impact of minor fluctuations on the overall temperature difference calculations.

In one embodiment the temperature measurement is recorded after a stable temperature is reached. A stable temperature is attained when the minimum temperature differs by no more than 3%, preferably no more than 2%, more preferably by no more than 1% of the total range of temperature In one embodiment the determining comprises correlating the temperature difference to the void fraction from a curve of temperature difference as a function of void fraction. Void fractions can be in the range of 0.1-0.7 and temperature differences can range from 5-25 degree units. The range of temperature change can correlate to flow rate of the two-phase fluid. High velocity flow rate results in a greater average temperature between the initial heated hollow tube temperature and the tube temperature in presence of fluid flow. Low velocity flow rate results in a lower average temperature between the initial heated hollow tube temperature and the tube temperature in presence of fluid flow. A threshold is selected to delineate high flow rate and low flow rate which can vary and is determined by the specific system parameters, heat transfer coefficients, and types of fluids familiar to one of ordinary skill in the art. The standard curves and dynamic range can be modeled to adjust for heat transfer coefficients and types of two-phase fluids familiar to one of ordinary skill in the art. This methodology may be useful in a range of 80 gallons/minute to 1200 gallons/minute, 100 gallons/minute to 1000 gallons/minute, and 200 gallons/minute to 800 gallons/minute. This methodology may be useful for a flow velocity in a range from 0.05 m/s/to 15 m/s, 0.1 m/s to 12 m/s, 0.2 m/s to 10 m/s, 0.5 m/s to 8 m/s, and 1 m/s to 5 m/s.

The method of the present disclosure uses relatively inexpensive mechanical parts and the principle of thermal conductivity of a solid to liquid and a solid to gas to resolve the void fraction of fluid flow. The implications of the method are improved preparations for piping systems for oil wells for fluid movement, early diagnoses of potential blockages, and early diagnoses for maintenance issues. This method to determine void fraction can be useful to continuously monitor and control the fluid movement in the piping systems of an oil well and reservoirs until blockages, flow rate issues, and maintenance issues are addressed and the fluid movement returns to normality. Additionally, this method to determine void fraction may be used in the establishment of new piping systems and to reconfigure piping systems to improve overall function and efficiency.

The invention claimed is:

1. An apparatus comprising:
   a temperature sensing device comprising a plurality of thermocouples having a sensing tip and wiring that is connected to a potentiometer;
   a hollow tube, wherein the sensing tips of the thermocouples pass through the inner wall of the hollow tube and extend radially from the hollow tube to contact the outer wall at different locations along the length of the hollow tube;
   a heat flux source that is connected to the hollow tube, wherein the heat flux source heats the walls of the hollow tube;
   wherein the hollow tube is inserted through a cross section of a pipe perpendicular to a longitudinal axis of the pipe such that no more than 80% of the hollow tube is within the interior of the pipe relative to the total length of the hollow tube;
   wherein a ratio of the hollow tube outer diameter to inner diameter is at least 3:2, a ratio of the hollow tube longitudinal length to outer diameter is at least 39:4, and a ratio of the inner diameter of the hollow tube to the inner diameter of the pipe is at least 1:3; and wherein the apparatus measures a void fraction in a two-phase liquid-gas mixture flowing through the pipe.

2. The apparatus of claim 1, wherein the hollow tube is at least 1 inch in inner diameter.

3. The apparatus in claim 1, wherein the hollow tube is secured to the pipe by a threaded coupling fitting.

4. The apparatus in claim 1, wherein at least a portion of the hollow tube is covered by a thermal insulation material.

5. The apparatus in claim 1, wherein the wiring of the thermocouple is aligned with the longitudinal axis of the hollow tube and flush with the interior wall of the hollow tube.

6. The apparatus in claim 1, wherein the wiring of the thermocouple is insulated.

7. The apparatus of claim 1, further comprising an external thermocouple located outside of the hollow tube and within the interior of the pipe, which measures the external temperature of the tube.

8. The apparatus of claim 1, which has at least 4 thermocouples.

9. The apparatus of claim 1, wherein the heat flux source produces at least 0.5 kW of power.

10. The apparatus in claim 1, further comprising an electronics housing unit comprising the potentiometer connected to the thermocouples and a heat flux controller connected to the heat flux source.

11. The apparatus in claim 10, further comprising:
a computer connected to the potentiometer and the heat flux controller.

12. The apparatus of claim 1, wherein the two-phase liquid-gas mixture is selected from a hydrocarbon, a heat transfer fluid, an aqueous fluid, or a combination thereof.

13. A method of measuring void fraction in a two-phase liquid-gas mixture comprising:
heating the hollow tube of claim 1 to a temperature in the range of 20° C.-34° C. to form a heated hollow tube;
recording a baseline temperature measurement on the outer surface of the heated hollow tube before liquid-gas mixture flow through the pipe and a temperature measurement from the plurality of thermocouples on the outer wall of the heated hollow tube in the presence of liquid-gas mixture flow through the pipe;
calculating the difference between the baseline temperature measurement and the temperature measurement in the presence of liquid-gas mixture flow; and
determining the void fraction in the two-phase flow of liquid-gas mixture through the pipe based on the calculated difference.

14. The method of claim 13, wherein the calculating further comprises averaging the temperature measurements of the outer wall of the hollow tube from the plurality of thermocouples.

15. The method of claim 13, wherein the temperature measurement is recorded after a stable temperature is reached.

16. The method of claim 13, wherein the determining comprises correlating the temperature difference to the void fraction from a curve of temperature difference as a function of void fraction.

* * * * *